(12) United States Patent
Opheim

(10) Patent No.: US 6,346,231 B1
(45) Date of Patent: Feb. 12, 2002

(54) FLAVORED GELATIN CAPSULE AND METHOD OF MANUFACTURE

(76) Inventor: Joar Opheim, 226 Kingsbury Dr., Aptos, CA (US) 95003

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/416,017

(22) Filed: Oct. 6, 1999

(51) Int. Cl.⁷ ............ A61K 9/48; A61K 9/66; A61K 9/64; A61K 35/66

(52) U.S. Cl. .......... 424/45; 424/455; 424/456; 424/523

(58) Field of Search ............... 424/455, 456, 424/451, 452; 514/54

(56) References Cited

U.S. PATENT DOCUMENTS

| | | | | |
|---|---|---|---|---|
| 4,744,988 A | * | 5/1988 | Brox | 424/456 |
| 4,888,239 A | * | 12/1989 | Brox | 428/402.2 |
| 5,141,961 A | * | 8/1992 | Coapman | 514/629 |
| 5,444,054 A | * | 8/1995 | Garleb et al. | 514/54 |
| 5,738,871 A | * | 4/1998 | Story | 424/451 |
| 5,874,418 A | * | 2/1999 | Stella et al. | 514/58 |
| 6,004,582 A | * | 12/1999 | Faour et al. | 424/473 |

* cited by examiner

*Primary Examiner*—Thurman K. Page
*Assistant Examiner*—Isis Ghali
(74) *Attorney, Agent, or Firm*—Howard E Lebowitz

(57) ABSTRACT

A flavored gelatin capsule and the method of manufacture of the flavored capsule is provided. The capsule may comprise (a) from about 10 to about 70 parts by weight of gelatin; (b) from about 10 to about 35 parts by weight of a suitable polyol, such as glycerol; (c) from about 8 parts by weight of water; and (c) various parts by weight of particular water soluble flavorings. The contents of the capsule may also be flavored. The composition is particularly useful in improving the palatability of fish oil medicinals.

18 Claims, 2 Drawing Sheets

FLAVORED GELATIN CAPSULE AND METHOD OF MANUFACTURE

BACKGROUND OF THE INVENTION

1. Field of the Invention

This invention relates to capsule formulations, medicinal and nutritive dose encapsulations and methods of manufacture of capsules. More specifically, the invention introduces flavoring into the manufacture of capsules and encapsulated doses.

2. Conventional Art

The taste of many medicinal and nutritive components can be quite distinctive and potentially unpleasant. Improvements in the taste of certain drugs and nutritional supplements can lead to a higher compliance by consumers. A higher compliance will result in greater commercial success for the drug and supplement manufacture and in increased health and well being particular consumers.

Taste is both a matter of purely subjective preference. Yet human taste is also strongly influenced by experience and cultural impressions. Broad generalizations about consumer taste presence can thus sometimes be relied upon in predicting market acceptance of specific drug and nutritive formulations. In Norway, for example the tastes of fish oils are far more palatable than in the United States. As a consequence of this United States market aversion to the taste of fish oils, many residents of the United States are less willing to ingest fish oils and will therefore not benefit from the nutritional and medicinal qualities of fish oils.

Yet the composition of certain fish oils includes elements that are identified in medical literature as providing significant health benefits. Polyunsaturated fatty acids, to include long chain Omega 3 fatty acids such as eicosapentaenoic add (EPA) and docosahexaenoic acid (DHA) are present in the livers of lean fish and other tissues of fatty fish. The human body cannot synthesize these fatty acids nor can it derive them from other fatty acids. As these fatty acids provide both medicinal and nutritional benefits, an intake of up two grams per day has been recommended by certain medical authorities.

It is suspected that Eicosanoids derived from EPA might have an anti-inflammatory effect on humans. It has been suggested that EPA might decrease blood levels of TG lipids, increase blood levels of high density lipids (HDL), decrease blood clotting, reduce the incidence of cardiac arrhythmia and stabilize heart rhythm.

It has been suggested that DHA may also decrease blood levels of TG lipids, increases blood levels of high density lipids (HDL). Furthermore, DHA might lower blood pressure, attack early phases of inflammation, facilitate the growth, development and function of the central nervous system and improves the clinical symptoms of depression and schizophrenia.

Increasing the consumption of recommended doses of certain Omega-3 fatty acids might therefore have a medically and nutritionally beneficial affect on many consumers and patients. Yet conventional techniques to improve the palatability of fish oils and other subjectively harsh tasting substances are limited in the prior art to the addition of flavorings into a mixture of the substances themselves. The flavoring of capsules of encapsulated formulations has been absent in the conventional art.

OBJECTS OF THE INVENTION

It is therefore an object of the present invention to provide a method of manufacture of gelatin capsules.

It is another object of the present invention to provide a gelatin capsule comprising a flavor.

It is an additional object of the present invention to optionally provide a flavored gelatin capsule containing a fish oil.

It is an yet another object of the present invention to optionally provide a flavored gelatin capsule containing a flavored fish oil.

SUMMARY OF THE INVENTION

These and other objects and advantages of the present invention are achieved by providing a flavored gelatin capsule comprising a water soluble flavor. The flavored gelatin capsule may include about 10 to about 70 parts by weight of a gelatin, about 10 to about 35 parts by weight of a glycerol, about 8 to about 35 parts by weight of a moisturizer and about 1 parts by weight of the water soluble flavoring. The flavoring of the capsule improves the taste and palatability of the capsule and will subjectively improve the taste of the gelatin and a dose or contents contained within the flavored gelatin capsule to individual consumers or patients.

The flavor may be one of, or a combination of suitable flavors known in the art, to include berry, strawberry, chocolate, cocoa, vanilla, lemon, nut, almond, cashew, macadamia nut, coconut, blueberry, blackberry, raspberry, peach, lemon, lime, mint, peppermint, orange, banana, chili pepper, pepper, cinnamon, and pineapple.

The gelatin capsule composition may include a polyol, such as sorbitol, glycerol or other suitable softening agent known in the art.

A preferred embodiment of the present invention includes flavoring the contents of the gelatin capsule in addition to flavoring the gelatin capsule. In particular, an oil soluble flavoring may be optionally mixed with a fish oil that is encapsulated within the capsule. The oil soluble flavoring may be similar to the taste of the flavor of the capsule, e.g., strawberry and strawberry, or the taste of the oil flavoring may be complementary to the capsule flavoring, e.g., banana and strawberry.

Fish oil containing Omega 3 fatty acids such as eicosapetaenoic acid (EPA) and docosahexaenoic acid (DHA) are one appropriate subject of inclusion into certain preferred embodiments of the present invention as are other digestible oils. The capsule of these certain preferred embodiments is flavored and the fish oil may optionally be flavored.

The method of the present invention includes the manufacturing process steps of combining gelatin, a glycerol or a ployol like sorbitol as a softener, water or a moisturizer containing water, a flavoring agent and optionally a coloring agent such as a titanium oxide, keratin or other suitable coloring agent known in the art.

Modified vegetable starch is substituted for gelatin in certain preferred embodiments of the present invention. Where gelatin is used, the gelatin may be a suitable mammalian or fish gelatin known in the art. The suitable gelatin or vegetable starch selected is used as a principal forming agent of the capsule.

DETAILED DESCRIPTION OF THE PREFERRED EMBODIMENTS

In describing the preferred embodiments, certain terminology will be utilized for the sake of clarity. Such terminology is intended to encompass the recited embodiment, as well as all technical equivalents which operate in a similar manner for a similar purpose to achieve a similar result.

Figure 1:
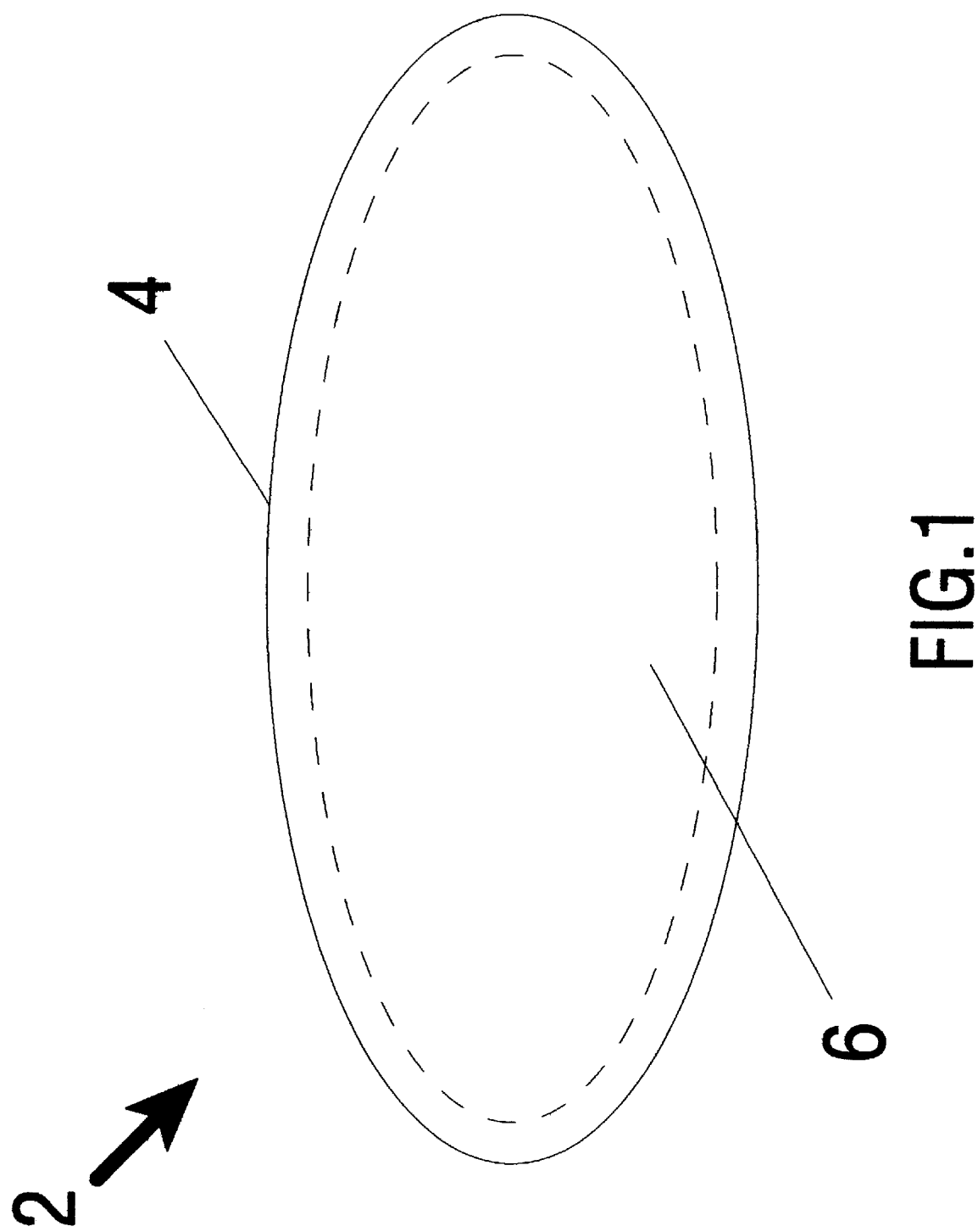
FIG. 1 is a flavored gelatin capsule containing a fish oil dose.

Referring now to FIG. 1, an encapsulated composition of a gelatin capsule and fish oil 2, or fish oil capsule 2, is formed by the encapsulation of a dose of fish oil 6 by a gelatin capsule 4. The gelatin capsule 4 is made of gelatin, glycerol, water, a flavoring and optionally a coloring agent. The fish oil dose 6 includes 180 mg of EPA and 120 mg of DHA.

Figure 2:
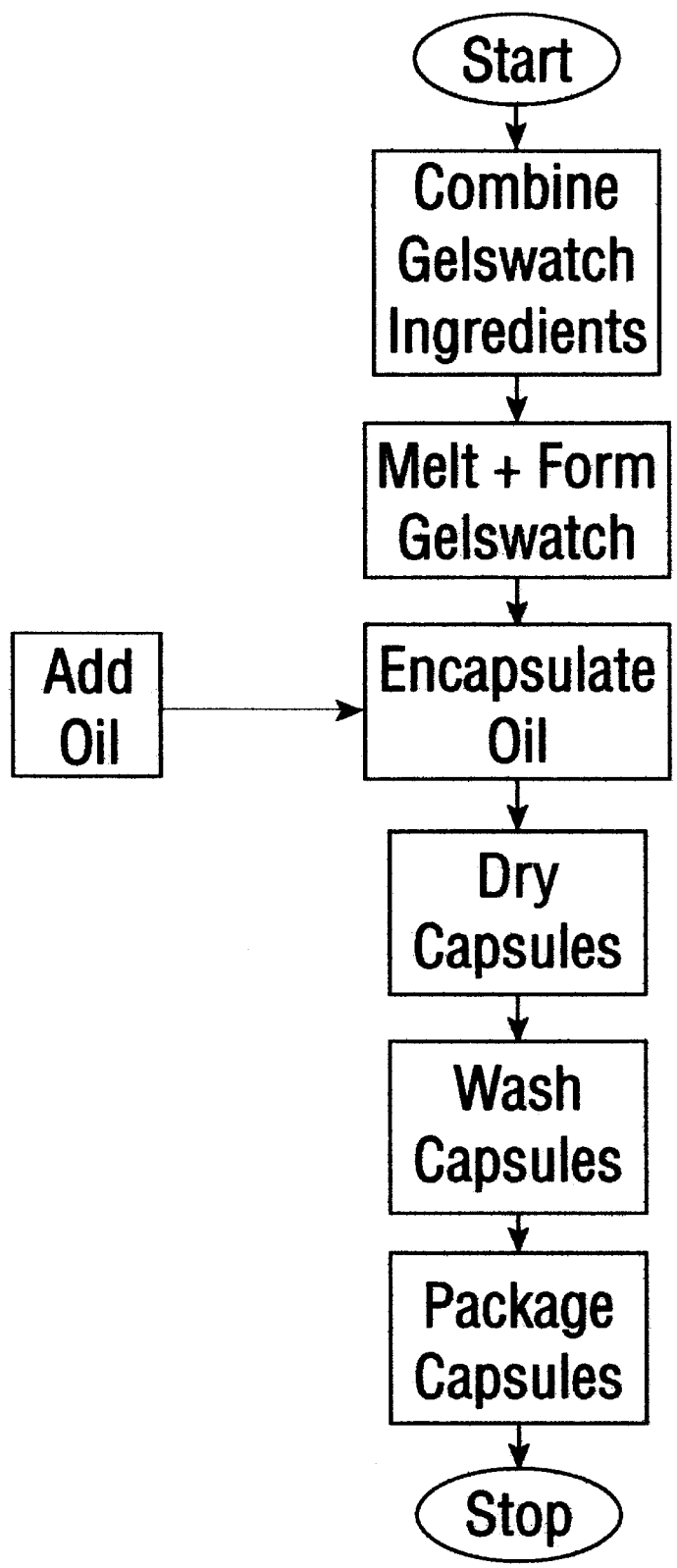
FIG. 2 is manufacturing process flow chart illustrating an embodiment of the method of the present invention.

Referring now to FIGS. 1 and 2, the manufacturing process of the preferred embodiment 2 of includes the steps of combining gelswatch ingredients, melting and forming a liquefied gelswatch, delivering the liquefied gelswatch and the fish oil 6 to an encapsulation machine, encapsulating a dose of fish oil, drying the encapsulated dose, washing the encapsulated dose and packaging the fish oil capsules 2 for shipment.

The gelswatch ingredients may include gelatin or a gelatin substitute such as modified starch or other suitable gelatin substitute known in the art, a softener such as glycerol or sorbitol or other suitable polyol or other gelatin softener known in the art, a flavoring agent such as strawberry flavor Firmenich #52311A or other suitable gelatin capsule flavoring known in the art and optionally a coloring agent such as keratin or other suitable gelatin capsule coloring agent known in the art.

The preferred embodiment 2 may be formed from a gelswatch mixture of 45 parts by weight of gelatin, 20 parts by weight of glycerol, 35 parts by weight of water and 0.5 or more parts by weight of strawberry flavor Firmenich #52311A. The gelswatch ingredients are then heated to about 60 degrees to 70 degrees Celsius and mixed together. The capsule is made of the gelswatch material. The liquefied gelswatch and the fish oil 6 is then poured into an encapsulation machine. The encapsulation machine then forms the fish oil capsule 2 comprising the fish oil dose 6 encapsulated by the gelatin capsule 4.

In certain alternate preferred embodiments of the present invention the range of water parts initially combined with the gelswatch may range from about 10 parts by weight to about 45 parts by weight; the amount of gelatin initially combined into the gelswatch may range from 10 parts by weight to about 70 parts by weight; and the amount of glycerol or other suitable softener known in the art may range from about 10 parts by weight to about 35 parts by weight.

The capsule composition 2 comprises about 500 milligrams of the fish oil dose 6 and about 240 milligrams of capsule 4 as formed from the gelswatch.

The fish oil capsule composition 2 is then dried at a temperature of about 20 degrees Celsius. The water content of the gelatin capsule is reduced to about 6% to about 12%, and preferably about 8%+/−2% by evaporation during the drying process step. The capsule 2 is then washed and packaged for shipment.

Experimental testing of the effects of varying amounts of the flavoring in both the capsule 4 and the fish oil 6 has shown that a concentration of 0.5% in the fish oil 6 of the Firmenich #52311A flavor will degrade in less than a year's span to below a desirable level of potency to the average North American consumer. Levels of 1 part by weight are preferred in order to extend the effective shelf life of the composition 2 beyond one year.

In addition, stream of commerce testing of concentration levels of Firmenich #52311A has shown that a level in excess of about 1.0 part by weight of the Firmenich #52311A in the capsule 4 provides an unexpected increase in the palatability of the composition 2 by generating a flavored bouquet from the capsules 2, whereby the consumer is greatly encouraged to ingest the composition 4 in a favorable response to his or her olfactory appreciation of the bouquet.

Certain preferred embodiments comprise fish oil presenting concentrations of Omega 3 fish as high or higher than 80% of the total weight of the dose 6, wherein the fish oil may include 50% DHA of the total weight of the dose 6, 20% EPA of the total weight of the dose 6 and about 10% by weight of other Omega 3 compounds. The concentration levels of the flavoring additive of a fish oil dose may, in certain preferred embodiments of the present invention having about 80% by weight of Omega 3 components, is reduced to from about 0.25% by weight to about 0.50% by weight of the dose 6.

Those skilled in the art will appreciate that various adaptations and modifications of the just-described preferred embodiments can be configured without departing from the scope and spirit of the invention. Therefore, it is to be understood that, within the scope of the appended claims, the invention may be practiced other than as specifically described herein.

What is claimed is:

1. A fish oil capsule for palatable presentation of fish oil comprising:
   a) a gelatin capsule, said gelatin capsule comprising gelatin, a gelatin softener, water, and a water soluble flavoring, wherein said water is present in said gelatin capsule in a concentration between about 6% and about 10%, and wherein said water soluble flavoring is present in a concentration between about 0.50% and about 1.50% of said gelatin capsule; and
   b) a fish oil dose, said gelatin capsule encapsulating said fish oil dose, whereby said fish oil capsule is a palatable fish oil composition which promotes ingestion of the fish oil.

2. The fish oil capsule claimed in claim 1, wherein said water soluble flavoring is present in a concentration between about 0.5% and about 1.0% of said gelatin capsule.

3. The fish oil capsule claimed in claim 1, wherein said water soluble flavoring is chosen from the group consisting of berry, strawberry, chocolate, cocoa, vanilla, lemon, nut, almond, cashew, macadamia nut, coconut, blueberry, blackberry, raspberry, peach, lemon, lime, mint, orange, banana, chili pepper, pepper, cinnamon, and pineapple.

4. The fish oil capsule claimed in claim 2, wherein said water soluble flavoring is chosen from the group consisting of berry, strawberry, chocolate, cocoa, vanilla, lemon, nut, almond, cashew, macadamia nut, coconut, blueberry, blackberry, raspberry, peach, lemon, lime, mint, orange, banana, chili pepper, pepper, cinnamon, and pineapple.

5. The fish oil capsule claimed in claim 3, further comprising an oil soluble flavoring, wherein said oil soluble flavoring is dissolved in said fish oil dose.

6. The fish oil capsule claimed in claim 4, further comprising an oil soluble flavoring, wherein said oil soluble flavoring is dissolved in said fish oil dose.

7. The fish oil capsule claimed in claim 5, wherein said oil soluble flavoring is chosen from the group consisting of berry, strawberry, chocolate, cocoa, vanilla, lemon, nut, almond, cashew, macadamia nut, coconut, blueberry, blackberry, raspberry, peach, lemon, lime, mint, orange, banana, chili pepper, pepper, cinnamon, and pineapple.

8. The fish oil capsule claimed in claim 6, wherein said oil soluble flavoring is chosen from the group consisting of berry, strawberry, chocolate, cocoa, vanilla, lemon, nut, almond, cashew, macadamia nut, coconut, blueberry, blackberry, raspberry, peach, lemon, lime, mint, orange, banana, chili pepper, pepper, cinnamon, and pineapple.

9. The fish oil capsule claimed in claim 7, wherein said oil soluble flavoring is present in a concentration between about 0.5% and about 1.0% of said fish oil dose.

10. The fish oil capsule claimed in claim 8, wherein said fish oil dose comprises at least one Omega-3 fatty acid chosen from the group consisting of eicosapentanoic acid and docosahexanoic acid.

11. The fish oil capsule claimed in claim 9, wherein said fish oil dose comprises at least one Omega-3 fatty acid chosen from the group consisting of eicosapentanoic acid and docosahexanoic acid.

12. A fish oil capsule for palatable presentation of fish oil comprising:
    a) a gelatin capsule, said gelatin capsule comprising gelatin, a gelatin softener, water, and a water soluble flavoring, wherein said water is present in said gelatin capsule in a concentration between about 6% and about 10%, and said water soluble flavoring is present in said gelatin capsule in a concentration between about 0.25% and about 0.50%, and wherein said gelatin capsule comprises between 10 and 35 percent of said gelatin softener, and said gelatin softener comprises at least one polyol, said polyol chosen from the group consisting of glycerol and sorbitol; and
    b) a fish oil dose, said gelatin capsule encapsulating said fish oil dose, whereby said fish oil capsule is a palatable fish oil composition which promotes ingestion of the fish oil.

13. The fish oil capsule claimed in claim 12, wherein said fish oil dose has a concentration of Omega-3 fatty acids above about 80%.

14. The fish oil capsule claimed in claim 13, wherein said water soluble flavoring is chosen from the group consisting of berry, strawberry, chocolate, cocoa, vanilla, lemon, nut, almond, cashew, macadamia nut, coconut, blueberry, blackberry, raspberry, peach, lemon, Iime, mint, orange, banana, chili pepper, pepper, cinnamon, and pineapple.

15. The fish oil capsule claimed in claim 14, further comprising an oil soluble flavoring, wherein said oil soluble flavoring is dissolved in said fish oil dose.

16. A process for forming a fish oil capsule for palatable presentation of fish oil, comprising the steps of:
    a) combining gelatin, a gelatin softener, water, and a water soluble flavoring;
    b) forming a gelswatch by heating, melting an mixing said gelatin, said gelatin softener, said water and said water soluble flavoring;
    c) forming a flavored capsule comprising a gelatin capsule encapsulating a fish oil dose with a portion of said gelswatch; and
    d) drying said flavored capsule to produce a water concentration in said gelatin capsule which is between about 6% and about 10%, and a water soluble flavoring concentration in said gelatin capsule above about 0.25%.

17. The process described in claim 16, wherein the water soluble flavoring is present in a concentration of between about 0.25% and about 1.25% of said gelatin capsule, and wherein an oil soluble flavoring is dissolved in said fish oil dose.

18. The process described in claim 16, wherein the water soluble flavoring is present in a concentration of between about 0.25% and about 1.0% of said gelatin capsule, and wherein an oil soluble flavoring is dissolved in said fish oil dose.

* * * * *